United States Patent
Firat et al.

(10) Patent No.: US 8,303,957 B2
(45) Date of Patent: Nov. 6, 2012

(54) MUTATED IMMUNOGENIC PEPTIDES DERIVED FROM R9M, POLYNUCLEOTIDES CODING FOR SAME AND THERAPEUTIC USES THEREOF

(75) Inventors: Hüseyin Firat, Paris (FR); Pierre Langlade-Demoyan, Paris (FR); Etienne Vilmer, Paris (FR); François Lemonnier, Bourg la Reine (FR); Pierre Rohrlich, Saint Mande (FR); Patricia Yotnda, Houston, TX (US)

(73) Assignee: Institut Pasteur, Paris (FR)

( * ) Notice: Subject to any disclaimer, the term of this patent is extended or adjusted under 35 U.S.C. 154(b) by 319 days.

(21) Appl. No.: 12/314,218

(22) Filed: Dec. 5, 2008

(65) Prior Publication Data

US 2009/0324556 A1    Dec. 31, 2009

Related U.S. Application Data

(60) Division of application No. 10/448,521, filed on May 30, 2003, now Pat. No. 7,476,719, which is a continuation of application No. PCT/FR01/03779, filed on Nov. 29, 2001.

(30) Foreign Application Priority Data

Dec. 1, 2000 (CA) .................................. 2325666

(51) Int. Cl.
*A61K 390/00* (2006.01)
(52) U.S. Cl. .................... 424/184.1; 514/1.1; 424/277.1
(58) Field of Classification Search .......................... None
See application file for complete search history.

(56) References Cited

PUBLICATIONS

Yotnda et al (J. Clin. Invest. vol. 102, p. 455-462, Jul. 1998.*
Yun et al (Tissue Antigens 54:153-161, 1999.*
Keogh et al, JI 167:787-796, 2001.*
Albert L. Lehninger et al., "Principles of Biochemistry", second edition, *Worth Publishers*, pp. 112-116 (1993).
P. Yotnda et al., "Cytotoxic T cell response against the chimeric ETVA-AML1 protein in childhood acute lymphoblastic leukemia", Jul. 1998, vol. 102, No. 2, pp. 455-462.
C. Yun et al., "Augmentation of immune response by altered peptide ligands of the antigenic peptide in a human CD4+ T-cell clone reacting to TEL/AML1 fusion protein", Mar. 1999, pp. 153-161.
Kawakami, Yutaka, et al., "Identification of new melanoma epitopes on melanosomal proteins recognized by tumor infiltrating T lymphocytes restricted by HLA-A1, -A2, and -A3 alleles", J. Immunology., 161:6985-6992 (1998).

* cited by examiner

*Primary Examiner* — Lei Yao
(74) *Attorney, Agent, or Firm* — Finnegan, Henderson, Farabow, Garrett & Dunner LLP

(57) ABSTRACT

The invention concerns the optimization of the wild R9M peptide and the use of the resulting peptides for therapeutic vaccination and/or preventive vaccination against leukaemia in humans. More particularly, the invention concerns mutated immunogenic peptides derived from the human TEL/AML1 fusion protein comprising the wild R9M peptide sequence Arg-Ile-Ala-Glu-Czs-Ile-Leu-Gly-Met. The invention also concerns polynucleotides coding for the mutated R9M immunogenic peptides, cellular expression vectors comprising nucleic acid sequences expressing the mutated R9M immunogenic peptides and polyclonal or monoclonal antibodies capable of being fixed on at least one of said peptides/polynucleotides. The invention further concerns the use of said peptides, polynucleotides and/or antibodies for preparing vaccines, anti-tumoral medicines and compositions and for in vitro and in vivo stimulation of the immune response in humans.

10 Claims, 4 Drawing Sheets

SEQUENCE LISTING

<160> NUMBER OF SEQ ID NOS: 45

<210> SEQ ID NO 1
<211> LENGTH: 9

```
<212> TYPE: PRT
<213> ORGANISM: Homo sapiens

<400> SEQUENCE: 1

Arg Ile Ala Glu Cys Ile Leu Gly Met
 1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Ile Ala Glu Ser Ile Leu Gly Met
 1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Ile Ala Glu Ala Ile Leu Gly Met
 1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Tyr Ile Ala Glu Ser Ile Leu Gly Met
 1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Ile Ala Glu Ala Ile Leu Gly Met
 1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: alpha-aminobutyric acid fixed to a glutamic
      acid

<400> SEQUENCE: 6
```

Arg Ile Ala Glu Xaa Ile Leu Gly Met
 1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: alpha-aminobutyric acid fixed to a glutamic
      acid

<400> SEQUENCE: 7

Tyr Ile Ala Glu Xaa Ile Leu Gly Met
 1               5

<210> SEQ ID NO 8
<211> LENGTH: 27
<212> TYPE: DNA
<213> ORGANISM: Homo sapiens

<400> SEQUENCE: 8
agaatagcag aatgcatact tggaatg                                         27

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
agaatagcag aaagcatact tggaatg                                         27

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
agaatagcag aaagtatact tggaatg                                         27

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
agaatagcag aatcaatact tggaatg                                         27

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 12
agaatagcag aatccatact tggaatg                                              27

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
agaatagcag aatcgatact tggaatg                                              27

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
agaatagcag aatctatact tggaatg                                              27

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
agaatagcag aagcaatact tggaatg                                              27

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
agaatagcag aagccatact tggaatg                                              27

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
agaatagcag aagcgatact tggaatg                                              27

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
```
agaatagcag aagctatact tggaatg                                          27

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tacatagcag aaagcatact tggaatg                                          27

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tatatagcag aaagcatact tggaatg                                          27

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tacatagcag aaagtatact tggaatg                                          27

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
tatatagcag aaagtatact tggaatg                                          27

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
tacatagcag aatcaatact tggaatg                                          27

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
tatatagcag aatcaatact tggaatg                                          27

```
<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
tacatagcag aatccatact tggaatg                                              27

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
tatatagcag aatccatact tggaatg                                              27

<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
tacatagcag aatcgatact tggaatg                                              27

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
tatatagcag aatcgatact tggaatg                                              27

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tacatagcag aatctatact tggaatg                                              27

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
tatatagcag aatctatact tggaatg                                              27

<210> SEQ ID NO 31
```

```
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
tacatagcag aagcaatact tggaatg                                            27

<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
tatatagcag aagcaatact tggaatg                                            27

<210> SEQ ID NO 33
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
tacatagcag aagccatact tggaatg                                            27

<210> SEQ ID NO 34
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonecotide

<400> SEQUENCE: 34
tatatagcag aagccatact tggaatg                                            27

<210> SEQ ID NO 35
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
tacatagcag aagcgatact tggaatg                                            27

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
tatatagcag aagcgatact tggaatg                                            27

<210> SEQ ID NO 37
<211> LENGTH: 27
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 37
tacatagcag aagctatact tggaatg                                              27

<210> SEQ ID NO 38
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
tatatagcag aagctatact tggaatg                                              27

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ala Met Pro Ile Gly Arg Ile Ala Glu
 1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Tyr Met Pro Ile Gly Arg Ile Ala Glu
 1               5

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Pro Ile Gly Arg Ile Ala Glu Cys Ile
 1               5

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Tyr Ile Gly Arg Ile Ala Glu Cys Ile
 1               5

<210> SEQ ID NO 43
```

-continued

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Tyr Ile Ala Glu Cys Ile Leu Gly Met
  1               5

<210> SEQ ID NO 44
<211> LENGTH: 9
<212> TYPE: PRT
<213> ORGANISM: Human immunodeficiency virus

<400> SEQUENCE: 44

Ile Leu Lys Glu Pro Val His Gly Val
  1               5

<210> SEQ ID NO 45
<211> LENGTH: 10
<212> TYPE: PRT
<213> ORGANISM: human herpesvirus

<400> SEQUENCE: 45

Phe Leu Pro Ser Asp Tyr Phe Pro Ser Val
  1               5                  10
```

MUTATED IMMUNOGENIC PEPTIDES DERIVED FROM R9M, POLYNUCLEOTIDES CODING FOR SAME AND THERAPEUTIC USES THEREOF

This application is a divisional of U.S. patent application Ser. No. 10/448,521, filed May 30, 2003, now U.S. Pat. No. 7,476,719, issued Jan. 13, 2009, which is incorporated herein by reference. U.S. Pat. No. 7,476,719 is a continuation of International Application No. PCT/FR01/03779, filed Nov. 29, 2001, which claims priority to Canadian Application No. 2,325,666, filed Dec. 1, 2000, in Canada.

CONTEXT OF THE INVENTION a) Field of the Invention

The present invention relates to the optimization of the wild type R9M peptide and to the use of the peptides obtained for therapeutic vaccination and/or preventive vaccination against leukemia in man. More particularly, the present invention relates to mutated R9M immunogenic peptides as antitumor agents against acute lymphoblastic leukemia (ALL).

b) Brief Description of the Prior Art

Acute lymphoblastic leukemia (ALL) is the most common cancer in children. About 450 new cases are treated every year in France. In spite of the progress of the chemotherapy protocols, 20% to 30% of these children have serious forms resistant to the conventional treatment or are cured at the price of the risk of severe toxicity. The progress relating to stem cell grafts and the greater accessibility of unrelated donors provide a cure for these patients only in certain cases. In this context, the search for therapeutic alternatives in the light of progress in immunology seems legitimate. The progress in antitumoral immunity can be applied to the field of the malignant hemopathies.

Antitumoral and Antileukemic Immunity

The identification of the epitopes of antigens associated with tumor cells has made it possible to develop new immunotherapeutic approaches applicable to human tumor pathologies. Many laboratories are thus engaged in the identification of tumoral epitopic peptides. While melanoma is the first illustration of the importance of this approach, it has now been extended with success to other tumor pathologies: cancer of the kidney, the bladder, the breast, the uterus and, more recently, the leukemias [Robinet et al. Hematother 7: 205-215, (1998); Rooney et al., Lancet, 345:9-13, (1995)] Clinical trials have already been initiated, using either synthetic epitopic peptides or recombinant viruses with encouraging results even though, in most cases, the characterization of the induced T lymphocyte responses could not be guaranteed.

The existence of an anti-leukemic immune response has been observed in the grafts of hematopoietic stem cells. In fact, the autologous or allogenic grafts depleted of T cells are associated with frequent relapses. On the other hand, the non T depleted grafts are associated with a higher risk of reaction of the graft against the host (GVHD) but that of relapse is lower: the graft thus has an anti-leukemic effect (GVL: graft versus leukemia). The role of the immune response in the malignant hemopathies has been confirmed by the remarkable but inconstant therapeutic effect of the transfusions of lymphocytes of the donor in the case of post-graft relapse particularly in the CML. The anergy induced by the absence of expression of B7 on the leukemic cells might explain why this GVL effect is more marked for the chronic myeloid leukemias (CML) than for the AML and the ALL. Nonetheless, several groups, including that of the applicant, have shown the existence of specific CTL against the leukemic cells of B type ALL and AML [Boyer et al., Blood, 89:3477-85, (1997); Buzyn et al., Europ. J. Immunol., 27:1066-72, (1997); Heslop et al., Nat. Med. 2:551-555, (1996); Yotnda et al., J. Clin Invest. 101:2290-6, (1998); Yotnda et al., J. Clin. Invest. 102:455-62, (1998)]. Thus, the applicant's group has demonstrated that chromosomal translocations can generate neo-antigens. In the case of the CML and the B-ALL with t (12;21), the fusion products BCR-ABL or TEL-AML1 expressed only on the leukemic cells induce specific CTL.

The TEL and AML1 Genes and the Translocation (p12; q21)

The translocation t(12;21) concerns 25% of the ALL of line B in children. It is normally demonstrated by molecular (RT-PCR) or in situ hybridization techniques (FISH). The TEL genes on chromosome 12 and the AML1 genes on chromosome 21 are implicated in this translocation. The TEL gene (Translocation ETS Leukemia) belongs to the family of the ETS genes which code for transcription regulatory factors [Fenrick et al., Mol. Cell. Biol. 20:5828-39 (2000)]. These proteins bind to specific sequences of the DNA through their ETS domain [Guidez et al., Blood 96:2557-61 (2000)]. Studies have shown an allelic loss of TEL in 15-40% of the cases of ALL of the B line of the child. This repressor gene is also implicated in the translocations t(5;12), t(9;12) and t(12;21) implicated in the malignant hemopathies.

The AML1 gene (Acute Myeloid Leukemia-1) belongs to a family of genes coding for transcription factors characterized by the presence of a binding domain to the DNA, the runt domain. The AML1 gene is composed of 9 exons. AML1 is expressed in all tissues with the exception of the heart and brain. It is assumed to code for a transcription factor implicated in the differentiation of the myeloid gene. This gene is usually associated with translocations t(8;21) and t(3;21) encountered in the acute myeloblastic leukemias.

The break point of the translocation t(12;21) is localized between the exons 5 and 6 of TEL and in the introns 1 or 2 of AML1. The fusion transcript TEL AML1 is always in the RNA of the lymphoblastic cells of patient carriers of the translocation (12;21) but never in normal tissues. This transcript is composed of the $NH_2$ terminus of TEL and almost the whole of AML1. Two transcripts of different lengths and the 5' end of which varies are produced. The longer form is present in the majority of the cases of ALL. The role of these fusion proteins still remains to be defined.

Clinical Aspects

The ALL of line B expressing the fusion gene TEL/AML1 affect children from 1 to 10 years of age who usually have less than 50,000 blasts at diagnosis, without hyperdiploidy on cytogenetic examination [Baruchel et al., Br. J. Hematol. 99: 101-106 (1997); Ma et al., Hematol. Oncol. 17:91-95 (1999)]. The presence of the transcript TEL/AML1 was associated with a diminution of the risk of relapse in several studies.

These studies must not mask the relative heterogeneity of these ALL: different publications as well as the personal experience of the present inventors suggest that about 15% of the cases of ALL with translocation (12;21) are characterized by their very poor prognosis without the mechanisms responsible for this being known [Seeger et al., Blood 91:1716-22 (1998)]. This population of children is particularly concerned by future protocols of immunotherapy.

Results in the Public Domain Obtained in the Laboratories of the Applicant

1) *Cytotoxic T response to the chimeric protein encoded in the TEL-fusion gene*[Yotnda et al., J. Clin. Invest. 102:455-62 (1998)]

The product of the chimeric genes resulting from the translocation (12;21) is a neoprotein which is expressed in the leukemic cells of common B-ALL type and which can be detected by Western blot. The applicant has postulated that peptides derived from this junction region might be tumor antigens recognized by cytotoxic effectors. In a first step, the capacity of 9 junctional nonapeptides to inhibit the binding to soluble HLA-A*0201 was measured. A nonapeptide RIAECILGM (R9M) (SEQ ID NO: 1) encoded in this fusion region was identified which possesses a high affinity for the soluble HLA-A2 molecule.

On diagnosis, before any treatment, in a HLA A2 patient carrier of the translocation (12;21) a CD8+T lymphocyte line was established from the bone marrow in the presence of autologous blast cells and the soluble form of the CD40 ligand. These T lymphocytes specifically lyse the autologous leukemia and recognize the peptide at the surface of the HLA-A*0201 targets loaded with the R9M peptide. Similar results are obtained at the clonal level. The set of data resulting from this study suggests that the R9M peptide of this translocation is immunogenic and induces in vitro specific T responses in the HLA-A*0201 patients.

However, the natural progression of the disease in spite of the existence of this immune response shows that the response developed is insufficient to control this tumor proliferation or that the tumor cells interfere negatively with the processes of activation and implementation of the cytotoxic response. The capacity of R9M to induce CTLs from the peripheral blood of healthy donors has been demonstrated. These specific CTL are capable of recognizing HLA-A*0201 targets pre-incubated with the peptide selected and they recognize leukemic cells expressing the fusion protein TEL-AML1 derived from HLA A2 patients.

2) *Absence of efficacious antitumoral response in the ALL* [Yotnda et al., *Exp. Hematol.* 27:1375-83, (1999)]

The expression of certain co-stimulatory molecules was studied at the surface of the lymphoblasts. In the majority of cases, the molecule B7.1 is absent from the surface of the blasts but is expressed in the presence of the soluble form of the CD40 ligand. It thus seems probable that the activation signals delivered to the T lymphocytes are insufficient [Dilloo et al., Blood 90:1927-33 (1997)]. This conclusion is supported by a certain number of complementary data taken from the direct study of the medullary CD3+T-lymphocytes at diagnosis. These lymphocytes have secretion profiles of type Th2 cytokines and are more frequently in apoptosis. This process of anergy of the specific CTLs has also been demonstrated in other tumoral pathologies [Boyer et al., Blood 89:3477-85 (1997); Dunussi-Joannopoulos et al., Blood 89:2915-24 (1997)].

Optimization of the Epitopic Peptides of the Fusion Region of TEL AML

The inventors of the present invention have observed that the R9M/HLA A2.01 complex at the surface of the T2 cells was quite unstable. Repeated attempts to immunize HLA A2.01 transgenic mice with the R9M peptide have also shown the inconstancy and the weakness of the CTL responses induced. It thus seems clear that the R9M peptide must be optimized in order to become an efficacious antitumor agent.

Hence there is a need for mutated R9M peptides possessing a high affinity for the HLA-A2.01 so as to form with this molecule a stable complex having a longer half-life than the half-life of the wildtype R9M peptide/HLA-A2.01 complex in order to render the peptide capable of inducing in vivo or in vitro a cytotoxic immune response.

There is also a need for mutated R9M peptides which can slow down the development of lymphoblastic tumor cells when administered to a leukemic patient.

More particularly, there is a need for mutated R9M peptides capable of inducing an immune response to the development of lymphoblastic tumor cells after administration to a receiver.

The present invention responds to these needs and to other needs as will become apparent to a person well acquainted with the field on reading the present description of the invention.

SUMMARY OF THE INVENTION

The present invention relates to the optimization of the wildtype R9M peptide and to the use of the peptides obtained for purposes of therapeutic vaccination and/or preventive vaccination against leukemia in humans.

More particularly, the invention relates to mutated immunogenic peptides derived from the human fusion protein TEL/AML1 comprising the wildtype R9M peptide sequence (Arg-Ile-Ala-Glu-Cys-Ile-Leu-Gly-Met) (SEQ ID NO: 1), the said peptides being mutated in the R9M peptide sequence. Preferably, the immunogenic peptides of the invention are characterized in that they slow down the development of lymphoblastic tumor cells and induce an immune response to the development of lymphoblastic tumor cells after their administration to a leukemic patient. Among the preferred peptides of the present invention are peptides having as peptide sequence: RIAESILGM (SEQ ID NO: 2), RIAEAILGM (SEQ ID NO: 3), RIAEα-butILGM (SEQ ID NO: 6), YIAESILGM (SEQ ID NO: 4), YIAEAILGM (SEQ ID NO: 5), and YIAEα-butILGM (SEQ ID NO: 7).

The invention also concerns the polynucleotides coding for the mutated immunogenic R9M peptides, the cellular expression vectors comprising the nucleic acid sequences expressing the mutated immunogenic R9M peptides and the polyclonal or monoclonal antibodies capable of binding to at least one of the peptides/polynucleotides previously mentioned.

The invention also relates to medicines and pharmaceutical compositions containing the peptides, the polynucleotides and/or the antibodies that are the objects of the invention.

The present invention also relates to the use of peptides, polynucleotides and/or antibodies such as defined above as anti-tumor agents for the preparation of an anti-tumor vaccine and for the stimulation in vitro and in vivo of the immune response in humans.

One of the major advantages of the present invention is that the mutated R9M peptides obtained possess a high affinity for the HLA-A2.01 molecule and form with this molecule a stable complex making them capable of inducing in vivo or in vitro a cytotoxic immune response.

Many other objectives and advantages of the present invention will become apparent on reading the non-limiting description of the invention which follows.

"Control" refers to the absence of R9M peptide.

"R9M" refers to the wild type R9M peptide (SEQ ID NO:1).

"R9M-5A" refers to an R9M peptide with a mutation in the fifth position replacing C with A (SEQ ID NO:3).

"Y9M-5A" refers to an R9M peptide with a mutation in the first position replacing R with Y and a mutation in the fifth position replacing C with A (SEQ ID NO:5).

"R9M-5S" refers to an R9M peptide with a mutation in the fifth position replacing C with S (SEQ ID NO:2).

"R9M-5S+1Y" refers to an R9M peptide with a mutation in the first position replacing R with Y and a mutation in the fifth position replacing C with S (SEQ ID NO:4).

"R9M-5a-but" refers to an R9M peptide with a mutation in the fifth position replacing C with alpha-aminobutyric acid which is linked to a glutamic acid (SEQ ID NO:6).

"R9M-5a-but+1Y" refers to an R9M peptide with a mutation in the first position replacing R with Y and a mutation in the fifth position replacing C with alpha-aminobutyric acid which is linked to a glutamic acid (SEQ ID NO:7).

Figure 4:
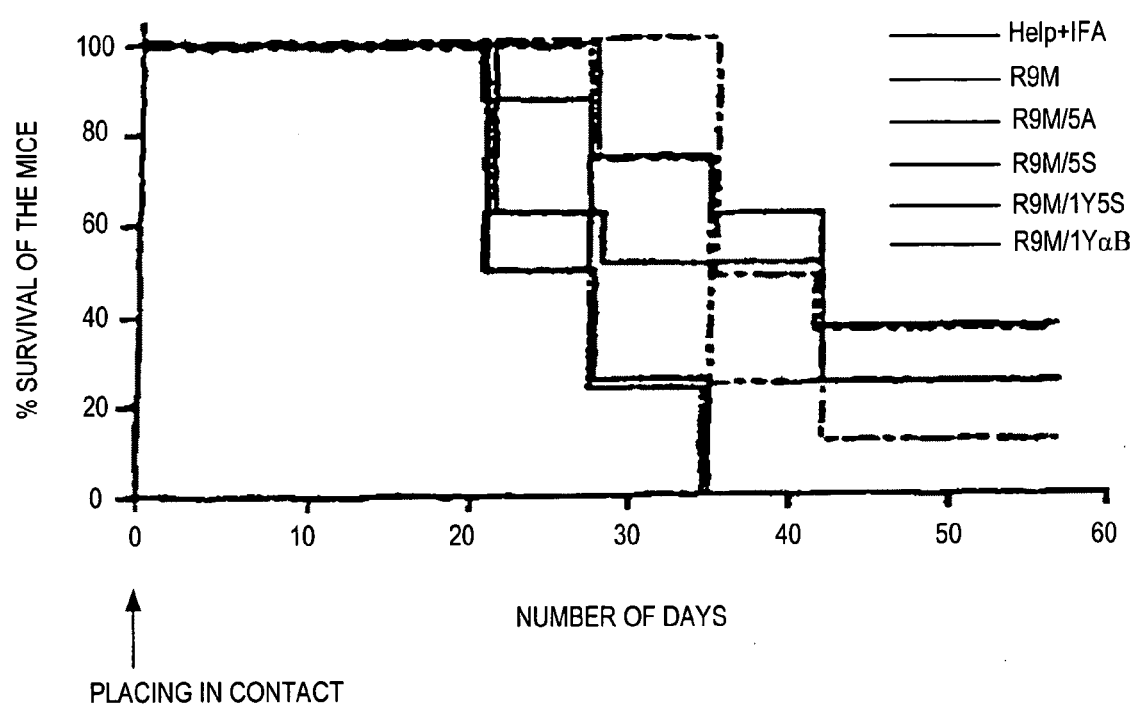

FIG. 4 illustrates the survival in percentage of HHD mice immunized with the wildtype R9M peptide (SEQ ID NO: 1) or the mutated R9M peptides (SEQ ID NOS 2, 4, 5 & 7, respectively, in order of appearance), the mice having tumors induced by EL4 S3-Rob-HHD cells expressing the TEL/AML1 fusion protein.

DETAILED DESCRIPTION OF THE INVENTION

The wildtype R9M peptide has the peptide sequence Arg-Ile-Ala-Glu-Cys-Ile-Leu-Gly-Met (RIAECILGM; SEQ ID No. 1). This peptide sequence corresponds to a region of the human fusion protein TEL/AML1 (GENBANK™ No. S78496).

The present invention relates to the optimization of the R9M peptide and to the use of the peptides obtained for therapeutic vaccination and/or preventive vaccination against leukemia in humans. The nomenclature used to describe the sequence of the peptides of the present invention is the international nomenclature using the three letter code or the one letter code, and in which the amino-terminus is presented on the left and the carboxyl terminus on the right.

It is advisable to point out that throughout the whole of the description "amino acid" is intended to designate both the natural amino acids and the non-natural amino acids. "Natural amino acid" is intended to designate the amino acids in the L form which can be found in the natural proteins, i.e. alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine.

However, the present invention also relates to the peptides having non-natural amino acids, i.e. the preceding amino acids in their D form as well as to the homo forms of certain amino acids like arginine, lysine, phenylalanine and serine or the nor forms of leucine or valine. In certain cases, it is advantageous to use alpha-aminobutyric acid and it is also possible to envisage the use of other amino acids like for example agmatine (Agm), alpha-aminoisobutyric acid (Aib), N-formyl-Trp (F-Trp), sarcosine, statin, ornithine, deamino-tyrosine and other modified amino acids. All the amino acids can be used provided they are not toxic to humans and that they do not modify the capacity of the peptides obtained to induce an immune response in vivo or in vitro.

By "peptide derivative" of a wildtype protein is meant all of the peptides which possess a peptide sequence substantially identical, at least in part, to the peptide sequence of the wildtype protein. They may be for example chemically modified peptides having a peptide sequence 100% identical with a portion of the wildtype protein. They may also be hybrid peptides having a first portion 100% identical with a first portion of the wildtype protein and a second portion in no way/partially identical with a second portion of the wildtype protein. They may also be peptides having a total/partial homology with a portion of the wildtype protein. According to a partial embodiment of the invention, the peptides comprise a peptide sequence derived substantially from the R9M peptide sequence of the human fusion protein TEL/AML1, this sequence having at least nine (9) consecutive amino acids.

By "mutated" peptides derived from a wildtype protein are meant all of the peptides which have been obtained following a modification of said wildtype protein, whether it is a modification by addition, deletion or substitution of one or more amino acids of the wildtype protein. It may also be a modification provided by the addition of carbon chains bound to at least one of the amino acids of the wildtype protein or to at least one of the amino acids of the peptides which corresponds to a substitution or a modification of one of the amino acids of the wildtype protein. More particularly, the present invention covers the peptides which derive from the human fusion protein TEL/AML1 which comprises the wildtype epitope R9M and which have been mutated in the R9M sequence. However, the present invention covers any polypeptide comprising a peptide sequence mutated or derived from the R9M wildtype sequence and capable of producing biological effects at least equivalent to those whose specific sequence is provided hereafter.

A person well-acquainted with the field of the invention will know how to obtain different mutated and derived peptides and will also know how to determine which of all of the peptides obtained are the peptides having adequate biological activity. Preferably, the sequence of the peptide (including its chemical modifications if necessary) will be such that the peptide obtained will possess an enhanced affinity for the HLA-A2.01 molecule such that it can form with this molecule a stable complex having a longer half-life ($DC_{50}$) than the half-life of the wildtype R9M peptide/HLA-A2.01 complex. The term $DC_{50}$ characterizing the half-life of the peptide HLA-A2.01 complex is described in the publication "H-2 class 1 knockout, HLA-A2.1-transgenic mice: a versatile animal model for preclinical evaluation of antitumor immunotherapeutic strategies" (European Journal of Immunology: 29:3112-21, 1999). This half-life ought normally to make it capable of inducing in vivo or in vitro a cytotoxic immune response. Preferably, the peptide obtained will slow down the growth of lymphoblastic tumor cells when administered to a leukemic receiver and will trigger a cytotoxic T response to the leukemic cells of common type B-ALL with t(12;21) of the leukemic receiver.

Advantageously, the inventors have discovered that the substitution of the amino acid cysteine at position 5 of the wildtype R9M peptide sequence by a neutral amino acid selected from serine, alanine and alpha-aminobutyric acid and/or the substitution of the amino acid arginine at position 1 of the wildtype R9M peptide sequence by an aromatic amino acid such as tyrosine conferred an enhanced biological activity on the mutated peptides. In this connection, the inventors have discovered that the peptides having as peptide sequence RIAESILGM (SEQ ID No. 2), RIAEAILGM (SEQ ID No. 3), YIAESILGM (SEQ ID No. 4), YIAEAILGM (SQ ID No. 5), RIAEα-butILGM (SEQ ID No. 6) and YIAE α-butILGM (SEQ ID No. 7), were particularly useful. By "α-but" is meant alpha-aminobutyric acid which is linked to glutamic acid.

It is also possible to make provision for other modifications (chemical or peptidic) making it possible for the peptides to cross certain biological barriers, to show a better solubilization, to facilitate their incorporation in special galenical forms such as for example liposomes or microparticles. Moreover, it is advisable to observe in this respect that the peptides according to the present invention may be available in a deglycosylated or glycosylated form if necessary.

The peptides according to the present invention can be prepared by any suitable procedure. In particular, they can be obtained by chemical synthesis but it is also possible to obtain them by a biological route by using, in particular, different vectors in suitable cell cultures such as will be described hereafter. It is also advisable to note that, in certain cases and depending on the method of preparation, it may be necessary to renature certain tertiary structures of the peptides obtained.

The DNA sequences coding for the peptides of the invention can be easily determined from the amino acid sequences. Table 1 gives the nucleotide sequence for the wildtype R9M peptide and the nucleotide sequences deduced for several mutated R9M peptides:

the peptide in the culture medium. Hence, the invention also relates to any cell host transformed by an expression vector such as defined above and comprising the regulatory elements permitting the expression of the nucleotide sequence coding for a peptide according to the invention. The use of vectors for the expression of proteins and peptides in the cells of a host, in particular the human host, is known and will not be described in detail. The specific constructions obviously depend on the host, the epitope and the vector selected.

The mutated peptides of the present invention and the polynucleotides encoding them can be used in many ways as antitumor agents or for the preparation of an antitumor vaccine. For example, they can be used in an in vitro stimulation procedure of the cytotoxic CD8 response, comprising the separation or not of the lymphoid cells of a patient and the incubation in vitro of the said cells in the presence of at least one mutated immunogenic peptide and/or in the presence of at least one polynucleotide, objects of the invention. Those cells which express the epitopes derived from TEL/AML1 can stimulate in vitro a specific anti-leukemic cytotoxic response, the CD8 T cells stimulated in vitro being subsequently injected into the leukemic patient. It is also possible to use the peptides and polynucleotides, objects of the invention, in an in vivo induction procedure of the anti-leukemic

TABLE 1

| PEPTIDE SEQUENCES | | NUCLEOTIDE SEQUENCE(S) | |
|---|---|---|---|
| SEQUENCE | SEQ ID NO: | SEQUENCE | SEQ ID NO: |
| RIAECILGM (wildtype R9M) | 1 | AGA ATA GCA GAA TGC ATA CTT GGA ATG | 8 |
| RIAESILGM | 2 | AGA ATA GCA GAA AGC ATA CTT GGA ATG | 9 |
| | | AGA ATA GCA GAA AGT ATA CTT GGA ATG | 10 |
| | | AGA AlA GCA GAA TCA ATA CTT GGA ATG | 11 |
| | | AGA ATA GCA GAA TCC ATA CTT GGA ATG | 12 |
| | | AGA ATA GCA GAA TCG ATA CTT GGA ATG | 13 |
| | | AGA ATA GCA GAA TCT ATA CTT GGA ATG | 14 |
| RIAEAILGM | 3 | AGA ATA GCA GAA GCA ATA CTT GGA ATG | 15 |
| | | AGA ATA GCA GAA GCC ATA CTT GGA ATG | 16 |
| | | AGA ATA GCA GAA GCG ATA CTT GGA ATG | 17 |
| | | AGA ATA GCA GAA GCT ATA CTT GGA ATG | 18 |
| YIAESILGM | 4 | TAC ATA GCA GAA AGC ATA CTT GGA ATG | 19 |
| | | TAT ATA GCA GAA AGC ATA CTT GGA ATG | 20 |
| | | TAC ATA GCA GAA AGT ATA CTT GGA ATG | 21 |
| | | TAT ATA GCA GAA AGT ATA CTT GGA ATG | 22 |
| | | TAC ATA GCA GAA TCA ATA CTT GGA ATG | 23 |
| | | TAT ATA GCA GAA TCA ATA CTT GGA ATG | 24 |
| | | TAC ATA GCA GAA TCC ATA CTT GGA ATG | 25 |
| | | TAT ATA GCA GAA TCC ATA CTT GGA ATG | 26 |
| | | TAC ATA GCA GAA TCG ATA CTT GGA ATG | 27 |
| | | TAT ATA GCA GAA TCG ATA CTT GGA ATG | 28 |
| | | TAC ATA GCA GAA TCT ATA CTT GGA ATG | 29 |
| | | TAT ATA GCA GAA TCT ATA CTT GGA ATG | 30 |
| YIAEAILGM | 5 | TAC ATA GCA GAA GCA ATA CTT GGA ATG | 31 |
| | | TAT ATA GCA GAA GCA ATA CTT GGA ATG32 | 32 |
| | | TAC ATA GCA GAA GCC ATA CTT GGA ATG33 | 33 |
| | | TAT ATA GCA GAA GCC ATA CTT GGA ATG34 | 34 |
| | | TAC ATA GCA GAA GCG ATA CTT GGA ATG35 | 35 |
| | | TAT ATA GCA GAA GCG ATA CTT GGA ATG36 | 36 |
| | | TAC ATA GCA GAA GCT ATA CTT GGA ATG37 | 37 |
| | | TAT ATA GCA GAA GCT ATA CTT GGA ATG38 | 38 |

Thus, the object of the invention is also a procedure for the preparation of a peptide of the invention by transformation of a cell host with the aid of an expression vector (plasmid, cosmid, virus, etc) comprising the DNA sequences coding for the peptides of the invention, followed by the placing in culture of the thus transformed cell host and the recovery of CD8 T response via the injection of cells expressing the epitopes derived from TEL/AML1 described previously into a leukemic patient, the injected cells permitting the induction of an anti-leukemic CD8 T response in vivo.

The mutated peptides of the present invention and the polynucleotides encoding them can also be used to prepare polyclonal or monoclonal antibodies binding to at least one peptide/polynucleotide object of the invention. The present invention thus also relates to such purified antibodies which can be obtained by very well known procedures.

The mutated peptides of the present invention and the polynucleotides encoding them can be used for the production of a medicine with the objective of being administered in vivo for the purposes of therapeutic and/or preventive vaccination against leukemia in humans, especially the common acute lymphoblastic leukemia B-ALL with t(12;21). These medicines may comprise at least one of the elements selected in the group constituted by the immunogenic peptides and the polynucleotides described above and lytic T-cells sensitized in vitro by the placing in contact of an immunogenic peptide according to the invention. The polyclonal or monoclonal antibodies previously mentioned may themselves also be used for the preparation of a medicine intended for the treatment of leukemia such as described hereafter.

In a privileged embodiment of the invention at least one portion of the immunogenic peptides/polynucleotides according to the invention is conjugated to a support to which it is absorbed or bound covalently or non-covalently at its C-terminus and/or N-terminus. The support may be constituted of carrier molecules (natural or synthetic), physiological and non-toxic. The carrier molecules can make it possible in particular to increase the immunogenicity of the peptides of the invention through the intermediary of complementary reactive groups borne respectively by the carrier molecule and the peptide. As an example of carrier molecules, mention should be made of natural proteins such as tetanus anatoxin, ovalbumin, serum albumins, hemocyamines, the PPD (purified protein derivative) of tuberculin, etc. As examples of synthetic macromolecular supports, mention should be made for example of the polylysines or the poly(D,L-alanine)-poly (L-lysine). As examples of hydrocarbon or lipid supports, mention should be made of the saturated or unsaturated fatty acids. The support may also take the form of liposomes, particles, vesicles, microspheres or latex or polystyrene beads.

The invention also relates to therapeutic compositions comprising a medicine or several polyclonal or monoclonal antibodies such as described previously and a pharmaceutically acceptable vehicle. These compositions may be advantageous for the treatment or the prevention of the common acute lymphoblastic leukemia B with t(12;21) in humans. Naturally, the use of antibody-based compositions usually requires that these latter are compatible with administration to humans. They may be, in particular, antibodies humanized by known procedures or directly expressed in situ from the DNA sequence.

The therapeutic compositions according to the present invention may be available in any solid or liquid form usual for pharmaceutical administration, i.e. for example forms of administration as liquid, as gel or any other support permitting for example controlled release. Of the usable compositions, mention may be made in particular of the injectable compositions more particularly designed for injection into the blood circulation in humans. The compositions of the invention may also contain constituents which increase the immunogenicity of the peptides, in particular other immunogenic peptides, specific or unspecific adjuvants of immunity such as Freund adjuvant, polysaccharides or equivalent compounds.

The present invention relates in addition to compositions designed to be administered in order to express in situ the peptides previously described. For example, by injecting the "naked DNA" coding for the immunogenic peptides of the invention, this injection leads in a certain number of cases to the expression of the encoded peptide and to an immune response to the said peptide. It will also be possible to use systems of "naked DNA" but which contain their proper expression system or expression vectors such as previously described. The expression vectors are likely, in certain cases, to improve the activity of the peptides expressed. The vaccination systems making use of the DNA sequences are known and have already been extensively described in the literature.

The invention also relates to tumor cells obtained by double transfection of EL4S3-Rob (murine β2-microglobulin negative) mice with:
1) the human gene encoding the HHD molecule; and
2) the human gene encoding for the fusion protein TEL/AML1 comprising:
   a) the wildtype R9M peptide sequence (Arg-Ile-Ala-Glu-Cys-Ile-Leu-Gly-Met) (SEQ ID NO: 1); or
   b) a mutated R9M peptide sequence coding for mutated immunogenic peptide such as defined above.

These cells make it possible to obtain an animal model of anti-leukemic vaccination, which validates the vaccination experiments. The methods for obtaining these kinds of cells are well known in the field and will not be described in detail. The method for obtaining the EL4 S3-Rob has been described in detail by Pascolo et al. in J. Exp. Med., 185:2043-51 (1997).

The present invention covers very particularly the cell line doubly transfected by the genes coding for the HLA-A2.01 and the TEL/AML1 translocation. This cell line is called "EL4 Rob.HHD.TEL.AML1" and was deposited as a biological sample with the National Culture Collection of Microorganisms (CNCM, Pasteur Institute, Paris) on 1 Dec. 2000, and was assigned the registration No. I-2587.

The invention also relates to a selection procedure for therapeutic molecules capable of inducing a protective immune response in vivo to fungal, bacterial, viral or tumoral wildtype peptides. This procedure is characterized in that:
  a) a tumor cell line, EL4S3-Rob, doubly transfected by nucleotide sequences coding for the HHD molecule and nucleotide sequences coding for the said fungal, bacterial, viral or tumor wildtype peptides is administered to an compatible animal model, the said animal model having a genotype compatible with that of said transfected tumor cell and having been previously immunized with the said molecules which it is desired to select;
  b) the capacity of the said transfected cells to induce a response in vivo to the epitopes of the said fungal, bacterial, viral or tumor peptides is compared with the capacity of the said fungal, bacterial, viral or tumor wildtype peptides to induce a response in vivo to the epitopes of the said wildtype peptides in an animal model subjected to prior immunization with the wildtype peptide sequences of the said therapeutic molecules.

In a preferential embodiment of the invention, the compatible animal model is obtained by using, on the one hand, a mouse having an inactive and unexpressed MHC replaced by the gene coding for HLA-A2.01 and, on the other hand, a tumor cell line transfected by at least the gene coding for the HLA-A2.01 molecule. It is, however, understood that the invention applies to any compatible animal model construction, for example by replacing the gene coding for HLA-A2.01 by a gene coding for HLA-B7 etc.

Although throughout the descriptive statement of the present invention the term "peptide" is used, it is understood that the invention is not limited to the compounds formed by the union of a limited number of amino acids. In fact, the flexibility of the recombinant technologies makes it possible to produce proteins comprising a multiplicity of identical or different epitopes and likely to improve the immunogenic activity of the final product. Thus the present invention also covers the immunogenic polymers comprising between two and ten peptides selected from the mutated peptides previously defined. Similarly, the present invention covers the polypeptides coding for a peptide sequence other than a wild-type R9M sequence, these polypeptides incorporating one or more peptide sequences coding for a peptide selected from the mutated peptides previously defined. Finally, the present invention includes the oligonucleotides having a nucleotide sequence coding for a peptide sequence other than a wildtype R9M sequence, these oligonucleotides incorporating one or more polynucleotides such as previously defined.

The examples described hereafter will make it possible to demonstrate other characteristics and advantages of the present invention.

EXAMPLES

The examples which follow serve to illustrate the useful range of the present invention and not to limit its scope. Modifications and variations can be made to it without departing from the spirit and scope of the invention. Although it is possible to use other methods or products equivalent to those that are found hereafter to test or carry out the present invention, the preferred materials and methods are described.

Example 1

Optimization of the Epitopic Peptides of the Fusion Region TEL/AML1

It is known that the affinity of an epitopic peptide for the MHC predicts in part its immunogenic potential. This affinity can be measured by its binding capacity to class I MHC and by the stability conferred on the peptide MHC complex thus formed at the cell surface by using tap T2 cells expressing HLA-A*02.01.

The inventors of the present invention observed that the R9M/HLA-A2.01 complex at the surface of the T2 cells was not very stable. These observations were related to the physico-chemical instability of the peptide due to the presence of a cysteine at position 5 susceptible to oxidation and the formation of by-products via the SH group. Recent articles show that the dimerization and the cysteinization of synthetic peptides containing cysteine occur in vitro but also in vivo and that these processes modify the immunogenicity of these peptides considerably. The presence of reducing agents or the replacement of cysteine by α-aminobutyric acid or serine increase the immunogenicity of these peptides.

Repeated attempts to immunize HLA A2.01 transgenic mice with the R9M peptide have shown the inconstancy and weakness of the CTL responses induced. The cysteine of the R9M peptide has thus been replaced by a neutral amino acid like serine or alanine or α-aminobutyric acid. The results above show that this replacement effectively increases the stability of the peptide-HLA-A*02.01 complex. The replacement of the amino acid at position 1 by a tyrosine also enables the immunogenicity of the restricted peptides HLA-A*0201 to be increased.

Figure 1:
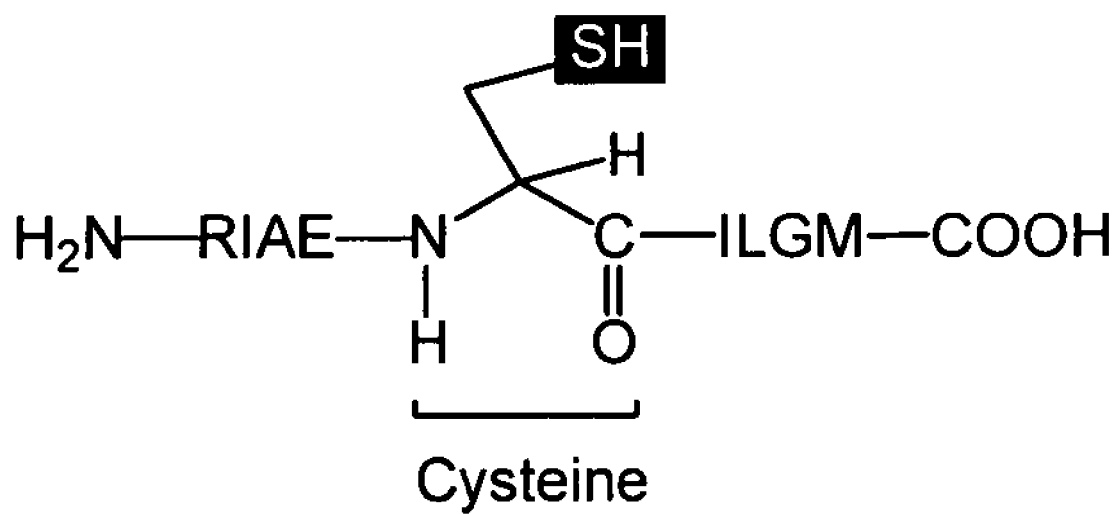
FIG. 1 shows the wildtype R9M epitopic peptide (SEQ ID NO: 1)

These preliminary results have subsequently been used to optimize further the R9M peptide. The results which follow show that the simple or double substitution at P5 by one of the neutral amino acids (alanine, serine or α-aminobutyric acid) and/or at P1 by tyrosine increases the antigenic capacities of these mutated peptides (FIG. 1). The binding tests performed in vitro by using the soluble HLA-A2.01 molecules and T2 cells have shown that the binding to and the stabilization capacity for the HLA-A2.01 molecules was greater than that of the wildtype R9M peptide (Table 2).

The immunogenicity of the mutated peptides was then studied in the HHD transgenic mouse (H2 class 1—negative and transgenic for HLA-A*02.01). These mice are described in European Journal of Immunology, 29:3112-21, 1999. Groups of more than 10 HHD mice were immunized by the synthetic peptides (emulsion in IFA with the helper peptide HBVcore128-140 as described previously in Firat et al., Eur. J. Immunol. 29:3112-21 (1999)).

Figure 2:
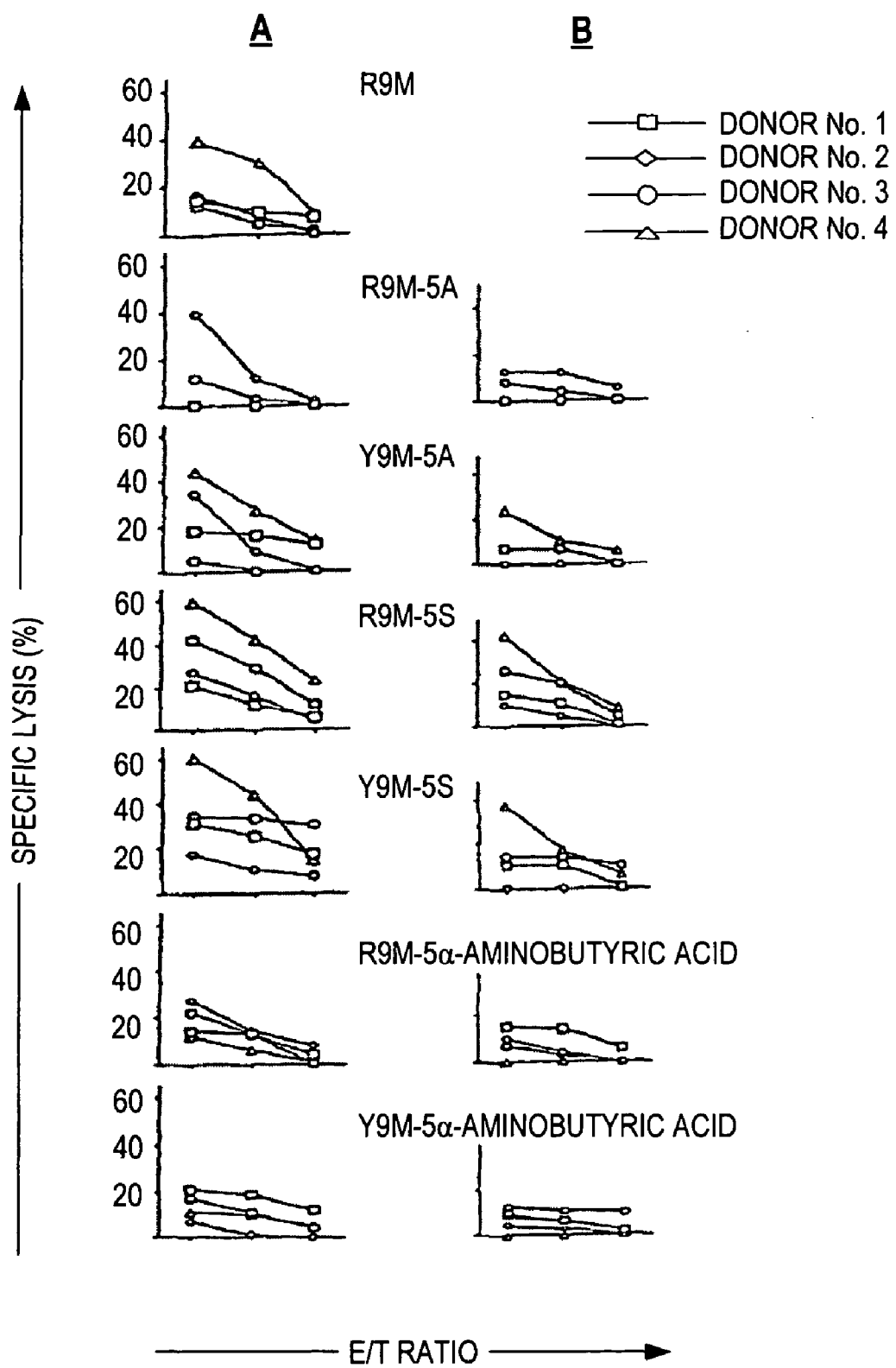
FIG. 2 (SEQ ID NOS 1-7, respectively, in order of appearance) illustrates with the aid of graphs the primary response of human CTL cells to HLA-A2.1*T2 target cells stimulated with different peptides. Column A=T2 cells stimulated with the mutated R9M peptides; Column B=T2 cells stimulated with the wildtype R9M peptide.

The HHD mice immunized by the native R9M peptide develop a weak specific CTL response nonetheless capable of recognizing the tumor line TEL AML* (Table 3 and Table 4). On the other hand, the mutated peptides (having single or double substitutions) induce a strong CTL activity and lyse the TEL AML* tumor lines in the majority of cases (Table 3 and Table 4). The enhanced immunogenicity of the mutated R9M peptides was then confirmed in vitro by using mononucleated cells of 5 healthy HLA-A*02.01 subjects (FIG. 2).

TABLE 2

Binding of the peptide derivatives of the native fusion protein ETV6-AMLT and their mutated analoque molecules to the HLA-A2.01 molecule.

| Peptide | Amino acid sequence | Measurement of stabilization | | Ratio peptide/$^{125}$I-F10V | |
|---|---|---|---|---|---|
| | | $RA^b$ | $DC50(h)^e$ | 10/1 | 25/1 |
| A9E | AMPIGRIAE (SEQ ID NO: 39) | 10-100 | 2-4 | $47^d$ | 57 |
| Y9E | YMPIGRIAE (SEQ ID NO: 40) | >100 | 0 | 39 | 47 |
| P91 | PIGRIAECI (SEQ ID NO: 41) | >100 | 0 | 23 | 58 |
| Y9I | YIGRIAECI (SEQ ID NO: 42) | >100 | <2 | 43 | 60 |
| R9M | RIAECILGM (SEQ ID NO: 1) | 2.9 | <2 | 64 | 69 |

TABLE 2-continued

Binding of the peptide derivatives of the native fusion protein ETV6-AMLT and their mutated analogue molecules to the HLA-A2.01 molecule.

| Peptide | Amino acid sequence | Measurement of stabilization RA[b] | DC50(h)[c] | Ratio peptide/$^{125}$I-F10V 10/1 | 25/1 |
|---|---|---|---|---|---|
| Y9M | YIAECILGM (SEQ ID NO: 43) | >100 | <2 | 45 | 66 |
| R9M-5A | RIAEAILGM (SEQ ID NO: 3) | 3.2 | <2 | 59 | 72 |
| Y9M-5A | YIAEAILGM (SEQ ID NO: 5) | 0.9 | 2-5 | 79 | 87 |
| R9M-5S | RIAESILGM (SEQ ID NO: 2) | 2.2 | 2 | 74 | 75 |
| Y9M-5S | YIAESILGM (SEQ ID NO: 4) | 1.4 | 2-5 | 25 | 37 |
| R9M-5α-but[a] | RIAEα-butLGM (SEQ ID NO: 6) | 2 | 2 | 27 | 49 |
| Y9M-5α-but[a] | YIAEα-butLGM (SEQ ID NO: 7) | 0.7 | 2-5 | 26 | 26 |
| HIV 1 rt.476 | ILKEPVHGV (SEQ ID NO:44) | 1 | 5 | NT | NT |
| F10V | FLPSDYFPSV (SEQ ID NO: 45) | NT | NT | 63 | 84 |

[a] Replacement of the cysteine residue by α-aminobutyric acid
[b] RA represents the ratio of the necessary concentrations of the sample tested versus the reference peptide to attain 20% of the maximal number of molecules stabilized such as defined with high concentrations of the reference peptide
[c] Half-life ($DC_{50}$) of the peptide-HLA-A2.1 stabilized complexes measured after an overnight incubation of the T2 cells and the reference peptide. Obtained by measuring by indirect immunofluorescence and a FACS analysis the residual cellular surface area of the peptide-HLA-A2.01 complexes at different intervals (0, 2, 4 and 5 h).
[d] Represents the percentage inhibition of the binding of the peptide of the hepatitis virus BHBVc.18-27 (F10V).

TABLE 3

Comparative study of the secondary response of the CTL cells derived from HHD mice immunized with the wildtype R9M peptide or the mutated R9M peptides

| | Effectors | |
|---|---|---|
| | RMAS-HHD cells stimulated with the mutated peptide [b]R/T (% of clear lysis) | [a]RMAS-HHD cells stimulated with the wildtype peptide [b]R/T (% of clear lysis) |
| R9M | 1/18 (13) | — |
| R9M-5A | 2/10 (40, 43) | 2/10 (22, 28) |
| Y9M-5A | 8/10 (27, 44, 51, 62, 65, 65, 66, 77) | 7/10 (11, 14, 18, 19, 34, 46, 50) |
| R9M-5S | 11/14 (15, 20, 24, 29, 37, 37, 39, 43, 64, 66, 72) | 6/14 (11, 11, 17, 50) |
| Y9M-5S | 9/10 (26, 35, 49, 52, 53, 57, 64, 65, 68) | 3/10 (14, 43, 45) |
| R9M-5a-but | 7/10 (14, 15, 30, 43, 52, 71, 75) | 5/10 (18, 32, 44, 58, 64) |
| R9M-5a-but | 8/10 (155, 45, 57, 58, 60, 62, 65, 67) | 8/10 (21, 29, 38, 46, 54, 54, 56) |

[a] Mouse spleen cells co-injected s.c. with the RM9 wildtype peptide and its mutated analogues and the helper peptide HBVc.128 in IFA eleven (11) days previously, were re-stimulated in vitro with different peptides. Six (6) days later the latter were evaluated at different E/T ratios against the RMA-S-HHD target cells possessing the different peptides as reference or a peptide control (inf.m.58).
[b] R/T represents the mice responders versus the total of mice tested. The mice were considered as having responded when at least 10% of specific lysis was observed. The values in parentheses correspond to the maximal lysis observed for each mouse responder at an E/T ratio 60:1.

TABLE 4

Comparative study of the tertiary response of CTL cells of HHD mice immunized with the wildtype R9WI peptide or the mutated R9M peptides

| | Effectors | |
|---|---|---|
| | RMAS-HHD cells stimulated with the mutated peptide $^b$R/T (% of clear lysis) | $^a$TEL/AML $^+$EL4-HHD cells $^b$R/T (% of clear lysis) |
| R9M | 2/10 (13, 25) | 5/10 (15, 15, 22, 30, 33) |
| R9M-5A | 1/10 (20) | 6/10 (17, 27, 32, 38, 43, 58) |
| Y9M-5A | 9/10 (10, 40, 44, 51, 62, 65, 66, 77) | 5/10 (15, 24, 24, 32, 34) |
| R9M-5S | 6/10 (20, 29, 39, 43, 64, 72) | 11/14 (12, 14, 15, 20, 24, 29, 31, 32, 34, 36, 56) |
| Y9M-5S | 9/10 (16, 26, 35, 52, 53, 57, 64, 65, 68) | 6/10 (13, 17, 22, 25, 32, 60) |
| R9M-5a-but | 8/10 (12, 25, 14, 15, 30, 43, 52, 71, 75) | 7/10 (11, 15, 25, 26, 31, 33, 43) |
| R9M-5a-but | 8/10 (18, 45, 65, 65, 68, 69, 69, 75) | 10/10 (11, 22, 28, 28, 31, 36, 39, 59, 69) |

$^a$Mouse spleen cells co-injected s.c. with the RM9 wildtype peptide and its mutated analogues and the helper peptide HBVc.128 in IFA eleven (11) days previously, were re-stimulated twice (2 times) in vitro with trophoblast-LPS possessing the reference peptides. The cells were evaluated six (6) days later at different E/T ratios against the RMA-S-HHD target cells possessing the different peptides as reference or a peptide control (inf.m.58) or against EL4-HHD cells expressing or not the tel/aml gene.
$^b$R/T represents the mice responders versus the total of mice tested. The mice were considered as having responded when at least 10% of specific lysis was observed. The values in parentheses correspond to the maximal lysis observed for each mouse responder at an E/T ratio 60:1.

Example 2

Development of a Tumor Model in the HHD Mouse

Figure 3:
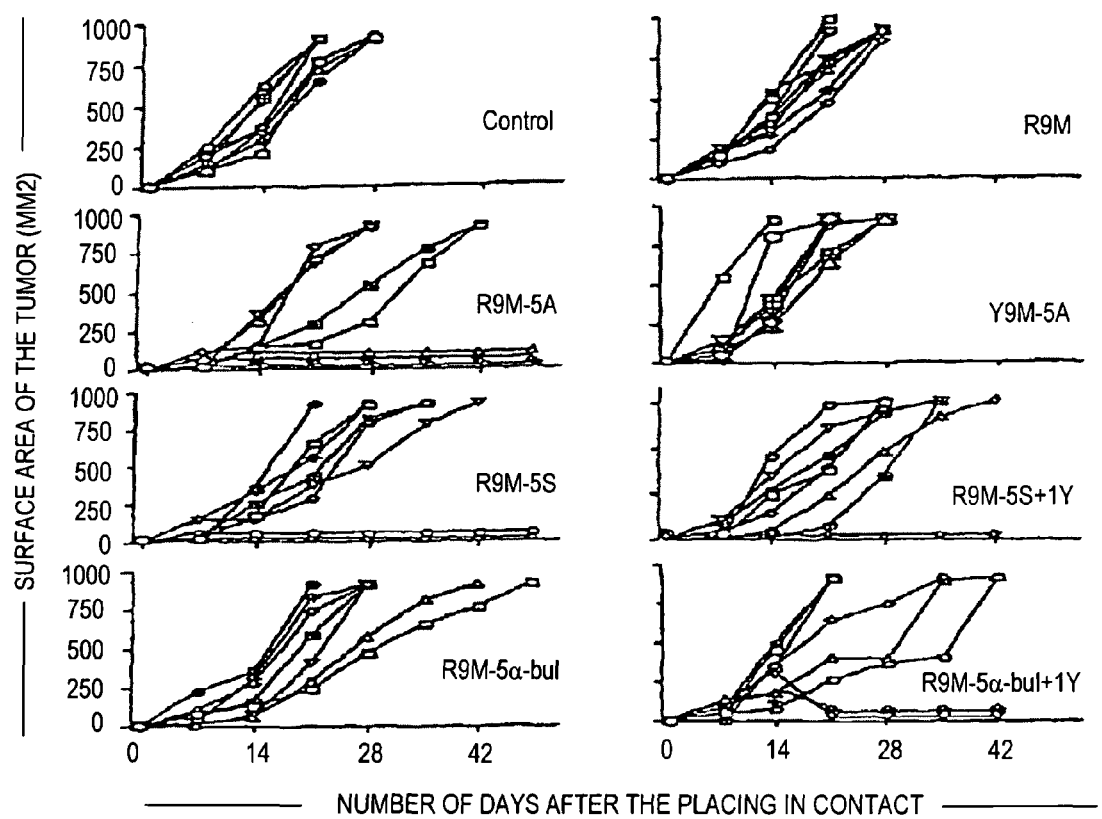
FIG. 3 (SEQ ID NOS 1-7) illustrates with the aid of graphics the induction of tumors in HHD mice by EL4 S3-Rob-HHD cells expressing the TEL/AML1 fusion protein.

The induction of a strong CTL response in vivo does not always reflect the protective capacity of this immune response against tumor cells. Thus, the tumor line EL4 S3-Rob (mouse β2-microglobulin negative) derived from C57Bl/6 mice and the same genetic base as the HHD mice, was doubly transfected by the HHD molecule and the TEL/AML1 gene. After successive passages, first in nude mice, then in HHD mice, the inventors have obtained a highly tumorigenic line in the HHD mouse. The injection of these tumor cells into groups of 8 HHD mice immunized beforehand with the wildtype R9M peptide or mutated R9M peptides has shown that only these latter, in particular R9M-5A, R9M-5α-butyric and R9M-5S were capable of slowing down the development of tumors (FIG. 3) and of prolonging the survival of the mice (FIG. 4). In certain mice, the inventors observed total protection.

Conclusion

The identification of epitopic peptides uniquely expressed by leukemic cells t(12;21) makes it possible to envisage an immunotherapeutic approach to patients. The present invention makes available methods and the biological material permitting the evaluation of vaccine preparations (animal model humanized for the restricted cytotoxic CD8 response, tumor model, series of optimized peptides).

Different strategies of immunization of HHD mice using the native R9M epitope and its mutated analogues will make it possible to further optimize the present invention in order to induce a strong and persistent response and to confer an efficacious protection without side effects. By using a biphasic strategy (murine exploratory phase, human validation phase), it will be possible to rapidly pre-select the vaccine formulations which can be proposed in the clinic. It will be possible to test the best mutated R9M peptides both alone and in combination in different vaccine vectors.

The passive immunotherapy approach consisting of reinjecting CTL induced in vitro into patients will also be able to be evaluated in HHD mice carriers of tumor EL4-S3-Rob-HD expressing the TEL-AML1 fusion protein.

It might also be possible to study the efficacy of the dendritic cells loaded with peptides or transduced in a stable manner because these cells are presently used in different human tumor diseases and seem to be efficacious in certain cases.

It will also be possible to evaluate the immunogenic potential of the polynucleotides coding for the mutated R9M peptides, either by injection of naked DNA or by the use of vectors. In fact, it is known that the chemical or viral vectors make it possible to increase the intensity of the immune response by better cell targeting and a prolongation of antigen presentation. Several vectors could therefore be used as vaccine vectors. Of the vectors which might be used, there are those recently developed at the Pasteur Institute, namely:

i) the vector pCMV-B10 encoding recombinant glycoproteins of the hepatitis B virus the immunotherapeutic effects of which in the treatment of cancer diseases have already been established;

ii) the recombinant measles vector generator of strong immune responses in individuals not already immune to measles;

iii) the triplex lentiviral vectors which induce in the mouse very efficacious memory and initial CTL responses and which are most efficient for inducing human responses in vitro after stimulation by dendritic cells;

iv) the recombinant ALVAC™ vector developed by Aventis-Pasteur; and v) the lipopeptides which are currently used in France in several clinical trials.

Although the present invention has been described with respect to concrete and preferred embodiments, it will however be obvious to persons trained in the art or science in question that it is possible to introduce a number of variations and modifications without departing from the scope of the invention described in this document.

The invention claimed is:

1. A method for in vivo stimulation of an immune response in a human patient having common B-type acute lymphoblastic leukemia (ALL) with t(12;21), comprising administering to the patient a mutated immunogenic R9M peptide in an amount sufficient to stimulate the immune response in the patient
wherein the mutated immunogenic R9M peptide consists of the amino acid sequence of SEQ ID NOS: 2, 3, 4, 5, 6, or 7.

2. A method according to claim 1, wherein the immune response stimulated with the mutated immunogenic R9M peptide is against the development of the common B-type ALL with t(12;21) after administration to the patient.

3. The method according to claim 1, wherein the immune response stimulated with the mutated immunogenic R9M peptide is a cytotoxic response against the common B-type ALL with t(12;21) cells of the patient.

4. The method according to claim 1, wherein the mutated immunogenic R9M peptide consists of the amino acid sequence of SEQ ID NO:2.

5. The method according to claim 1, wherein the mutated immunogenic R9M peptide consists of the amino acid sequence of SEQ ID NO:3.

6. The method according to claim 1, wherein the mutated immunogenic R9M peptide consists of the amino acid sequence of SEQ ID NO:4.

7. The method according to claim 1, wherein the mutated immunogenic R9M peptide consists of the amino acid sequence of SEQ ID NO:5.

8. The method according to claim 1, wherein the mutated immunogenic R9M peptide consists of the amino acid sequence of SEQ ID NO:6.

9. The method according to claim 1, wherein the mutated immunogenic R9M peptide consists of the amino acid sequence of SEQ ID NO:7.

10. A method for slowing down the growth of a tumor cell in a patient, comprising administering to the patient a mutated immunogenic R9M peptide in an amount sufficient to stimulate an immune response in the patient,
wherein the tumor cell is a leukemic cell of the common B-type ALL with t(12;21),
wherein the mutated immunogenic R9M peptide consists of the amino acid sequence of SEQ ID NOS: 2, 3, 4, 5, 6, or 7, and
wherein the mutated immunogenic R9M peptide slows down the growth of the leukemic cell of the common B-type ALL with t(12;21) after administration to the patient.

* * * * *

UNITED STATES PATENT AND TRADEMARK OFFICE
CERTIFICATE OF CORRECTION

PATENT NO. : 8,303,957 B2
APPLICATION NO. : 12/314218
DATED : November 6, 2012
INVENTOR(S) : Hüseyin Firat et al.

Page 1 of 1

It is certified that error appears in the above-identified patent and that said Letters Patent is hereby corrected as shown below:

Title page, item 73, "Assignee: Institut Pasteur (FR)" should read
--Assignees: Institut Pasteur, Paris (FR); Institut National De La Sante Et De La Recherche Medicale, Paris (FR); Assistance Publique-Hopitaux De Paris, Paris (FR)--.

Signed and Sealed this
Second Day of April, 2013

Teresa Stanek Rea
*Acting Director of the United States Patent and Trademark Office*